US010695102B2

(12) United States Patent
May et al.

(10) Patent No.: US 10,695,102 B2
(45) Date of Patent: Jun. 30, 2020

(54) SPINAL IMPLANT SYSTEM AND METHODS OF USE (71) Applicant: Warsaw Orthopedic, Inc, Warsaw, IN (US)

(72) Inventors: Jason M. May, Collierville, TN (US); William Alan Rezach, Covington, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 121 days.

(21) Appl. No.: 15/843,981

(22) Filed: Dec. 15, 2017

(65) Prior Publication Data
US 2019/0183536 A1 Jun. 20, 2019

(51) Int. Cl.
A61B 17/70 (2006.01)
A61B 17/00 (2006.01)

(52) U.S. Cl.
CPC ...... A61B 17/7037 (2013.01); A61B 17/7032 (2013.01); A61B 2017/00867 (2013.01)

(58) Field of Classification Search
CPC ............ A61B 17/7037; A61B 17/7032; A61B 2017/00867
See application file for complete search history.

(56) References Cited

U.S. PATENT DOCUMENTS

| 5,885,286 | A | 3/1999 | Sherman et al. |
|---|---|---|---|
| 6,565,566 | B1 | 5/2003 | Wagner et al. |
| 8,167,910 | B2 | 5/2012 | Nilsson |
| 8,197,518 | B2 | 6/2012 | Hammill et al. |
| 8,298,265 | B2 | 10/2012 | Purcell et al. |
| 8,304,089 | B1 | 11/2012 | Song et al. |
| 8,556,938 | B2 | 10/2013 | Jackson et al. |
| 2007/0270839 | A1 | 11/2007 | Jeon et al. |
| 2008/0108992 | A1 | 5/2008 | Barry et al. |
| 2011/0093021 | A1 | 4/2011 | Fenger et al. |
| 2015/0201972 | A1* | 7/2015 | Doubler ............. A61B 17/7002 606/266 |
| 2016/0317206 | A1* | 11/2016 | Rezach .............. A61B 17/7037 |
| 2017/0245898 | A1* | 8/2017 | May ................... A61B 17/7037 |
| 2017/0281241 | A1* | 10/2017 | Jackson ............. A61B 17/7037 |

FOREIGN PATENT DOCUMENTS

| JP | 2005169071 A | 6/2005 |
|---|---|---|
| KR | 2015010720 A | 9/2015 |
| KR | 20150107153 A | 9/2015 |
| KR | 1020150107153 A | 9/2015 |
| KR | 1020150107290 A | 9/2015 |

OTHER PUBLICATIONS

International Search Report and Written Opinion for PCT/US2018/065323, the US counterpart application dated Apr. 2, 2019, 17 pages.

* cited by examiner

Primary Examiner — Tessa M Matthews (57) ABSTRACT

A bone fastener comprises a first member defining an implant cavity and a plurality of adjacent grooves. A first band is configured for disposal within the grooves. A second band is configured for disposal within the grooves. A second member is configured to penetrate tissue and includes a head engageable with the first band to provisionally connect the members. A first part is engageable with a spinal rod disposed with the implant cavity. A second part is attached with the first part and engageable with the second band to dispose the second band adjacent the first band to fix connection of the members. Implants, systems, instruments and methods are disclosed.

20 Claims, 6 Drawing Sheets

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member defining an implant cavity and a plurality of adjacent grooves. A first band is configured for disposal within the grooves. A second band is configured for disposal within the grooves. A second member is configured to penetrate tissue and includes a head engageable with the first band to provisionally connect the members. A first part is engageable with a spinal rod disposed with the implant cavity. A second part is attached with the first part and engageable with the second band to dispose the second band adjacent the first band to fix connection of the members. In some embodiments, implants, systems, instruments and methods are disclosed.

In one embodiment, the bone fastener comprises a first member defining an implant cavity and a plurality of adjacent grooves including a first portion and a second portion having a greater diameter than the first portion. A first band and a second band are configured for disposal within the grooves in an expanded configuration in the second portion and a contracted configuration in the first portion. A second member is configured to penetrate tissue and includes a head engageable with the first band to connect the members. A first part is engageable with a spinal rod disposed with the implant cavity. A second part is attached with the first part and engageable with the second band to fix the second band adjacent the first band. The head is engageable with the second part to limit relative movement in a single plane.

In one embodiment, the bone fastener comprises a first member defining an implant cavity and a plurality of adjacent grooves including a first groove, a second groove and a third groove. The second groove has a greater diameter than the first groove and the third groove. A first expandable band is configured for disposal within the grooves. A second expandable band is configured for disposal within the grooves. A second member is configured to penetrate tissue and includes a head engageable with the first band for translation from the first groove to the second groove to provisionally connect the members. A first part is engageable with a spinal rod disposed with the implant cavity. A second part is attached with the first part and engageable with the second band for translation from the third groove to the second groove such that the second band prevents the first band from translating back into the second groove to fix connection of the members for relative movement in a single plane. In some embodiments, the second band engages the first band for translation to the second groove and restricts any further translation of the first band to fix connection of first member to second member.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a spinal implant system including a bone fastener. In one embodiment, the present spinal implant system includes an implant comprising a bone fastener, such as, for example, a pedicle bone screw. In some embodiments, the systems and methods of the present disclosure are employed with a spinal joint fusion or fixation procedure, for example, with a cervical, thoracic, lumbar and/or sacral region of a spine.

In some embodiments, the present spinal implant system comprises a modular bone screw having a restricted range of motion. In some embodiments, the present spinal implant system comprises a modular pedicle screw having a range of motion that is restricted to a single plane. In some embodiments, the present spinal implant system comprises modular pedicle screw that allows for uni-axial functionality. In some embodiments, the present spinal implant system comprises a modular bone screw system including a mechanism to resist and/or prevent disengagement of a retainer of a modular screw system. In some embodiments, the present spinal implant system comprises a modular bone screw system including a screw shank, a receiver, a retainer, a part, such as, for example, a crown and a part, such as, for example, a sleeve.

In some embodiments, the present spinal implant system comprises a bone screw having a crown that comprises commercially pure titanium alloy (Ti CP). In some embodiments, the crown is configured to provide an increase in axial grip on a spinal rod and an increase in flexion and/or extension strength. In some embodiments, the present spinal implant system comprises a bone screw having a sleeve that comprises cobalt chromium (CoCr). In some embodiments, the sleeve is configured to provide an increase in the rigidity of the connection between the sleeve and the screw shank to facilitate manipulation of patient anatomy with the bone screw.

In some embodiments, the present spinal implant system is employed with a method of attaching a head assembly with a screw shank including the steps of translating a screw shank such that a retainer translates from a first chamber into a second chamber and expands then contracts to provisionally capture the screw shank. In some embodiments, the method includes the step of, once the screw shank is provisionally captured, the compression member being translated towards an expansion member forcing the expansion member from a third chamber into the second chamber. In some embodiments, when the expansion member is fully in the second chamber it is allowed to expand. As such, the expansion member allows for the compression member to pass through its inner diameter in the expanded state. In some embodiments, the expansion member is sized to prevent the retainer from disengaging from the first chamber. In some embodiments, the retainer positioned in the first chamber is prevented from expanding and retains the screw shank in the head assembly.

In some embodiments, the present spinal implant system is employed with a method including the steps of inserting a screw shank into a receiver to contact a retainer translating the retainer from a first chamber to a second chamber. In some embodiments, the second chamber is oversized allowing for expansion of the retainer as the screw shank is translated into the receiver. In some embodiments, the spinal implant system comprises a modular pedicle screw system having an additional expansion member configured to block the second chamber after the screw shank is engaged with the receiver. In some embodiments, blocking of the second chamber resists and/or prevents the retainer from migrating back into the second chamber and resists and/or prevents disengagement of the components of a pedicle screw.

In some embodiments, the present spinal implant system comprises a modular assembly consisting of a receiver, expansion member, retainer and compression member. In some embodiments, the receiver includes first, second, and third chambers. In some embodiments, the first chamber is sized to be a close fit to a retainer member and the second chamber is oversized to allow expansion of the retainer. In some embodiments, the expansion of the retainer allows a screw shank to pass through the retainer. In some embodiments, a second expansion member is nested in an undersized third chamber, which causes the expansion member to collapse, such as, for example, by a reduction in diameter. The expansion member contains an outer groove, which mates with the receiver to prevent unintentional disengagement. In some embodiments, the expansion member in the relaxed state is sized with a diameter similar to the second chamber. In some embodiments, the spinal implant system includes a sleeve and a crown positioned above the expansion member.

In some embodiments, the spinal implant system comprises a modular system that includes a bone fastener including an array of members, such as, for example, bone screw shafts that can be selectively coupled to members, such as, for example, receivers. In some embodiments, the spinal implant system comprises a selectively coupled bone fastener that can be assembled on a surgical table or in-situ. In some embodiments, the bone fastener is selectively coupled with a non-instrumented and/or manual assembly. In some embodiments, the non-instrumented assembly comprises manually engaging a screw shaft with a head/receiver of the bone fastener. In some embodiments, the non-instrumented assembly comprises manually engaging the screw shaft in a pop-on engagement with the head/receiver of the bone fastener. In some embodiments, a force required to manually engage a screw shaft with a head/receiver of the bone fastener in a non-instrumented assembly is in a range of 2 to 50 N. In some embodiments, a force required to manually engage a screw shaft with a head/receiver of the bone fastener in a non-instrumented assembly is in a range of 5 to 10 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the head assembly includes a ring disposed with an implant receiver connected with a screw shaft assembly. In some embodiments, the ring is configured to snap onto the screw shaft assembly. In some embodiments, the ring has a minimized thickness and/or height to facilitate snapping the ring onto the screw shaft assembly. In some embodiments, the force required to snap the ring onto the screw shaft assembly is in a range of 2 to 50 N. In some embodiments, the force required to snap the ring onto the screw shaft assembly is in a range of 5 to 10 N.

In some embodiments, the bone fastener is configured for assembly without the use of an instrument, such as, for example, a practitioner, surgeon and/or medical staff utilizes their hands for assembly. In some embodiments, the system requires minimal force to attach an implant receiver and a screw shaft assembly in-situ thereby reducing a pre-load on the vertebrae, such as, for, example, the pedicle. In some embodiments, the bone fastener includes an expandable ring.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-8, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 180. Bone fastener 180 comprises a member, such as, for example, a screw shaft assembly 12 connectable with a member, such as, for example, a head assembly 13 in a configuration having a range of motion that is restricted to a single plane. In some embodiments, engagement of head assembly 13 and screw shaft assembly 12 allows for relative movement in a single plane forming a uni-axial bone fastener 180.

Head assembly 13 includes a band, such as, for example, a retaining ring 36 configured for provisional capture of screw shaft assembly 12 and/or fixed connection of the components of bone fastener 180, as described herein. Head assembly 13 includes a band, such as, for example, a ring 44 configured for disposal in a contracted orientation and an expanded interference orientation adjacent to ring 36 to facilitate fixed connection of the components of bone fastener 180. In some embodiments, screw shaft assembly 12 and head assembly 13 are assembled in situ or prior to implant to form bone fastener 180, as described herein.

Head assembly 13 includes a receiver 14. Receiver 14 extends along and defines an axis X1. Receiver 14 includes a pair of spaced apart arms 16, 18 that define an implant cavity 20 therebetween configured for disposal of a component of a spinal construct, such as, for example, a spinal rod (not shown).

Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone fastener 180. In some embodiments, arms 16, 18 are connected at proximal and distal ends thereof such that receiver 14 defines a closed spinal rod slot. In some embodiments, a spinal rod may be monolithically formed with receiver 14 or pre-assembled with receiver 14.

Cavity 20 is substantially U-shaped. In some embodiments, all or only a portion of cavity 20 may have alternate cross section configurations, such as, for example, closed, V-shaped, W-shaped, oval, oblong triangular, square, polygonal, irregular, uniform, non-uniform, offset, staggered, and/or tapered. Receiver 14 includes an inner surface 22. A portion of surface 22 includes a thread form 24 located adjacent arm 16 and a thread form 26 located adjacent arm 18. Thread forms 24, 26 are each configured for engagement with a coupling member, such as, for example, a setscrew (not shown), to retain the spinal rod within cavity 20. In some embodiments, surface 22 may be disposed with the coupling member in alternate fixation configurations, such as, for example, friction fit, pressure fit, locking protrusion/recess, locking keyway and/or adhesive. In some embodiments, all or only a portion of surface 22 may have alternate surface configurations to enhance engagement with the spinal rod and/or the setscrew, such as, for example, rough, arcuate, undulating, mesh, porous, semi-porous, dimpled and/or textured. In some embodiments, receiver 14 may include alternate configurations, such as, for example, closed, open and/or side access. In some embodiments, screw shaft assembly 12 is manually engaged with head assembly 13 in a non-instrumented assembly, as described herein, such that removal of head assembly 13 from screw shaft assembly 12 can withstand a clamp force applied from the coupling member.

Figure 6:
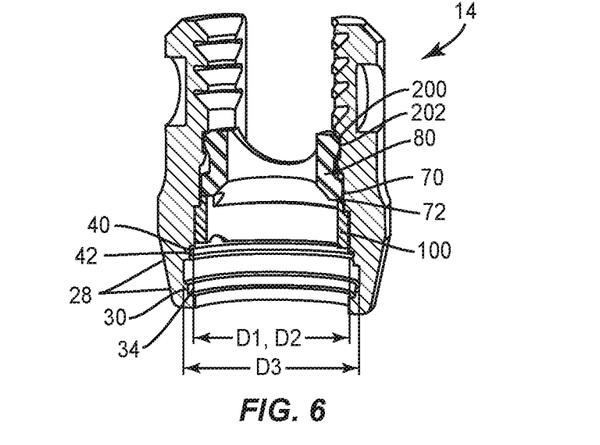
FIG. 6 is a perspective cross section view of components of one embodiment of a spinal implant system in accordance with the principles of the present disclosure.

Receiver 14 includes portion 28, as shown in FIG. 6. Portion 28 includes a surface 30. Surface 30 defines a cavity, such as, for example, a groove 34. Groove 34 is configured for disposal of ring 36. In some embodiments, groove 34 extends about all or a portion of surface 30. Groove 34 includes a diameter D1. Ring 36 includes a circumference that defines an opening, such as, for example, a gap. In some embodiments, the gap is sized such that the gap has a thickness that is less than the height and the width. In some embodiments, the gap is sized to allow ring 36 to pass though a bottom of receiver 14 by contracting circumferentially.

Portion 28 includes a surface 40, as shown in FIG. 6. Surface 40 defines a cavity, such as, for example, a groove 42. Groove 42 is configured for disposal of ring 44. Ring 44 includes a surface 46 that defines an outer groove 48 configured for engagement with a surface of groove 42, as described herein. Ring 44 includes a circumference that extends between ends of ring 44. In some embodiments, the ends define an opening, such as, for example, a gap. In some embodiments, the gap is sized such that the gap has a thickness that is less than the height and the width. In some embodiments, the gap is sized to allow ring 44 to engage surface 40 by contracting circumferentially.

Figure 7:
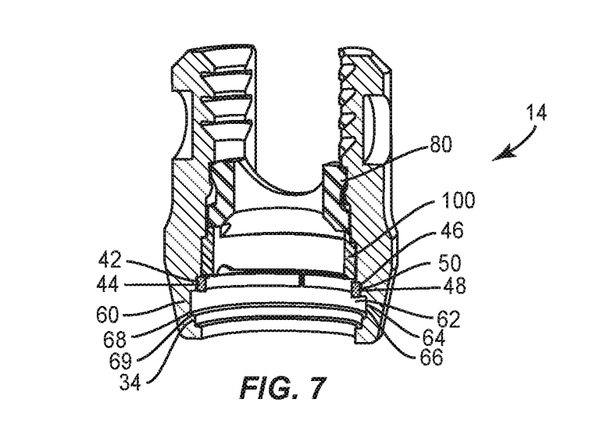
FIG. 7 is a perspective cross section view of components of the system shown in FIG. 6.

Groove 42 includes a projection 50. Projection 50 is configured for engagement with surface 46 of outer groove 48, as shown in FIG. 7. Projection 50 retains ring 44 within groove 42. Projection 50 is configured to resist and/or prevent disengagement of ring 44 from groove 42. Ring 44 is disengageable from groove 42 upon engagement with a part, such as, for example, a sleeve 100, which causes surface 46 to disengage from projection 50 and drives ring 44 from groove 42, as described herein. Groove 42 includes a diameter D2. In some embodiments, diameter D1 is equal to diameter D2, as shown in FIG. 6. In some embodiments, diameter D1 and diameter D2 are different. In some embodiments, surface 40 retains ring 44 within groove 42 and groove 42 does not include projection 50.

Figure 1:
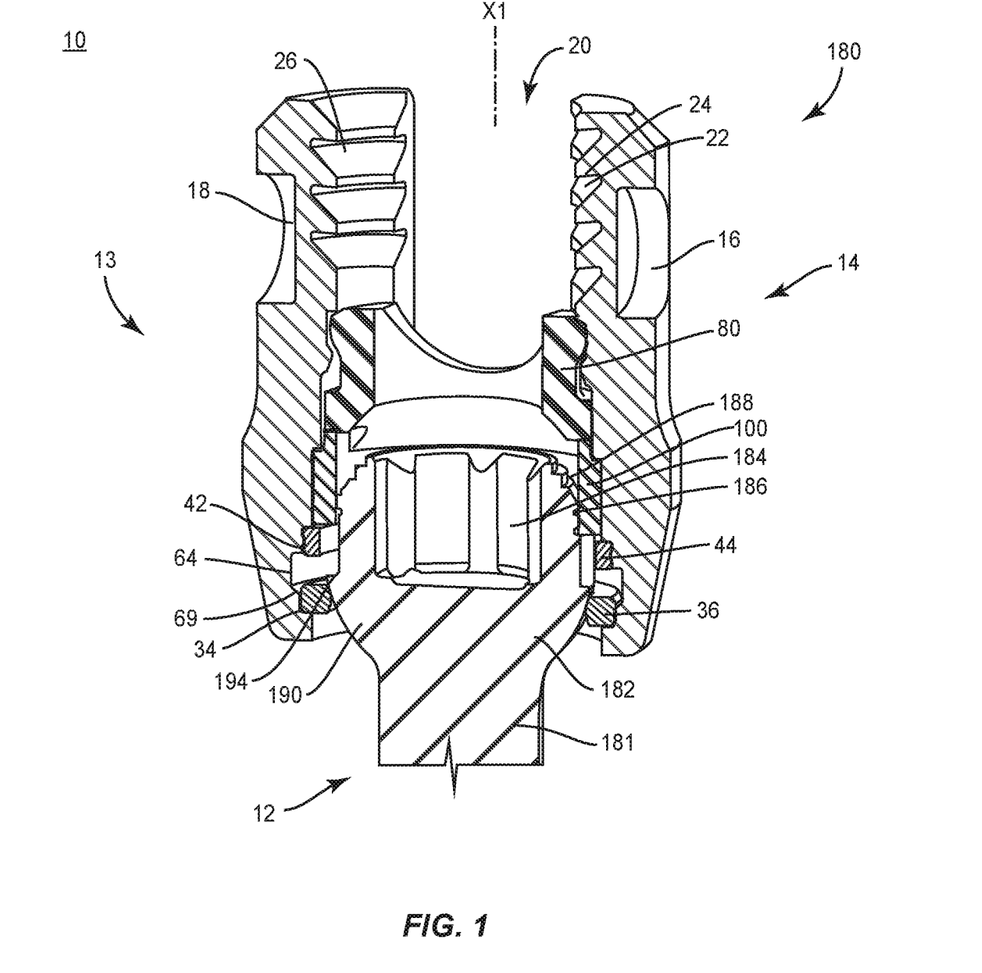
FIG. 1 is a perspective cross section view of components of one embodiment of a spinal implant system in accordance with the principles of the present disclosure.

Receiver 14 includes a portion 60, as shown in FIG. 7. Portion 60 includes a surface 62. Surface 62 defines a cavity, such as, for example, a groove 64 configured for disposal of ring 36 and/or ring 44. In some embodiments, groove 64 extends about all or a portion of surface 40. Groove 64 includes a circumferential channel 66 that accommodates expansion of ring 36 and/or ring 44, as described herein. Groove 64 includes a diameter D3. Diameter D3 is greater than diameter D1 and/or diameter D2. Diameter D3 is sized to allow for expansion of ring 36 and/or ring 44 therein. Grooves 34, 42, 64 are disposed in a serial orientation along axis X1, as shown in FIG. 1. In some embodiments, grooves 34, 42, 64 are disposed in spaced apart relation.

A surface 68 is disposed between groove 64 and groove 34, as shown in FIG. 7. Surface 68 is disposed at an angle relative to axis X1 to define a ramp 69. Ramp 69 is selectively inclined to facilitate translation of ring 36 between groove 34 and groove 64, as described herein. In one example, ring 36 is engaged with screw shaft assembly 12 for translation such that ring 36 slides along ramp 69, which directs and/or guides ring 36 from groove 34 into groove 64, and expands into a provisional capture orientation with screw shaft assembly 12. In another example, ring 36 is engaged with ring 44 for translation such that ring 36 slides along ramp 69, which directs and/or guides ring 36 from groove 64 into groove 34, and contracts for fixed connection of the components of bone fastener 180 including permanent capture of head assembly 13 and screw shaft assembly 12. In some embodiments, surface 68 is oriented substantially perpendicular to axis X1.

Figure 9:
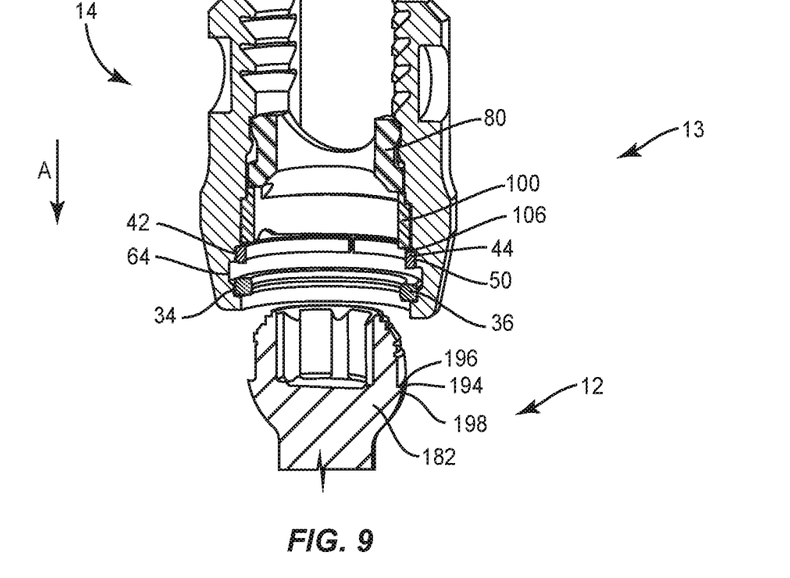
FIG. 9 is a perspective cross section view of components of one embodiment of a spinal implant system in accordance with the principles of the present disclosure.
Figure 10:
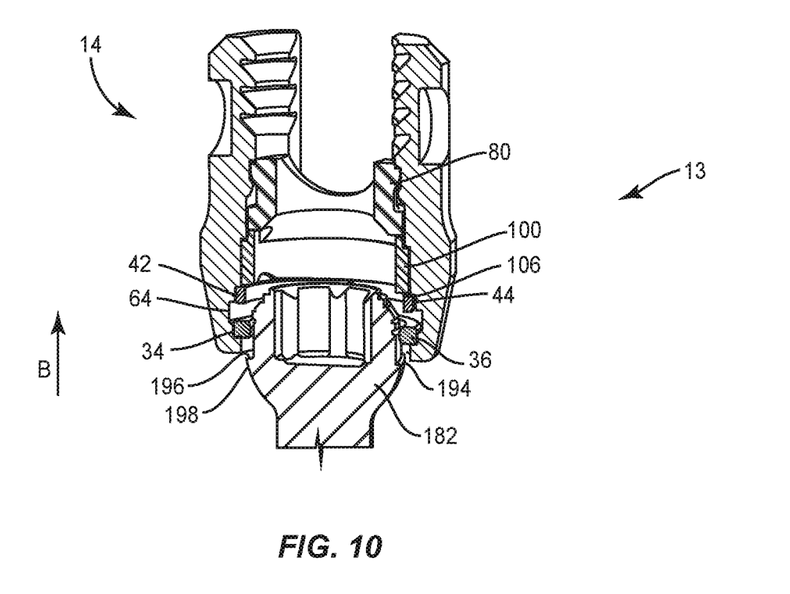
FIG. 10 is a perspective cross section view of components of the system shown in FIG. 9.
Figure 11:
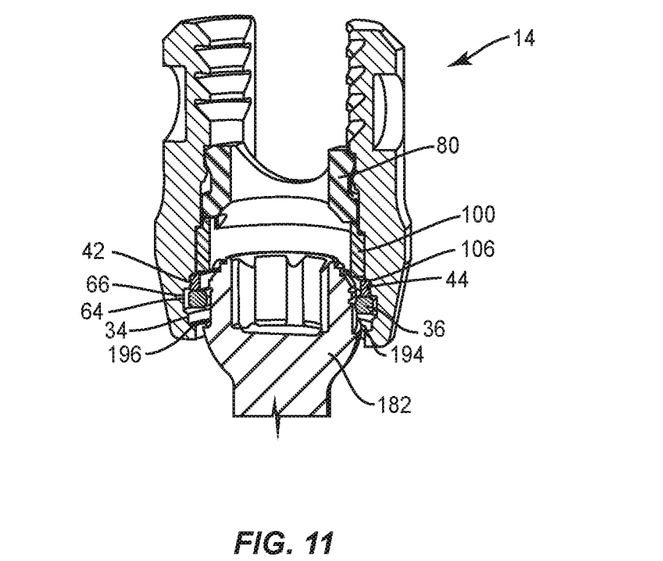
FIG. 11 is a perspective cross section view of components of the system shown in FIG. 9.
Figure 12:
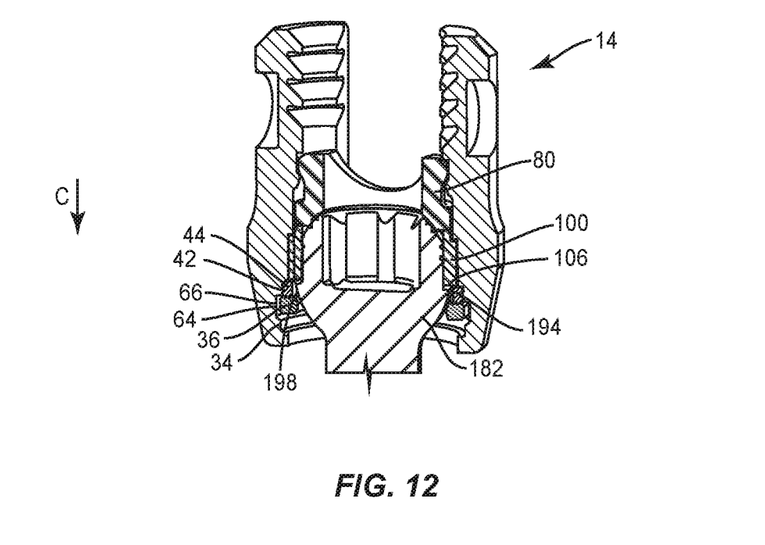
FIG. 12 is a perspective cross section view of components of the system shown in FIG. 9.
Figure 13:
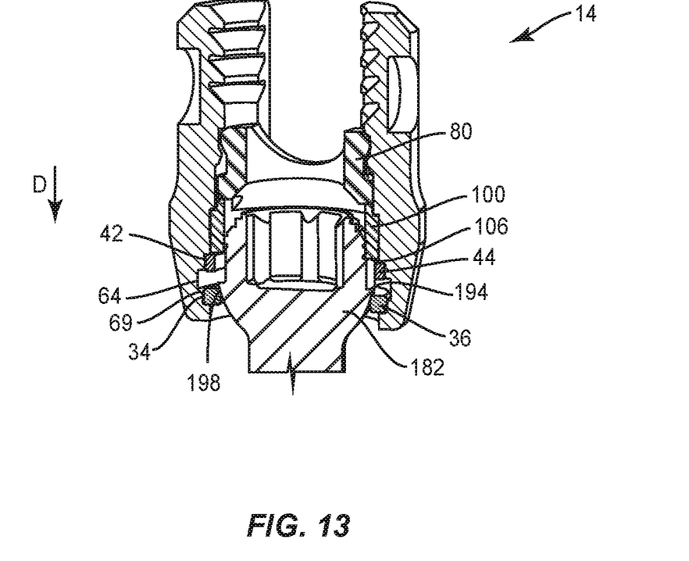
FIG. 13 is a perspective cross section view of components of he system shown in FIG. 9.

Ring 36 is resiliently biased to a contracted and/or capture orientation within groove 34, as shown in FIG. 9, and expandable to an expanded orientation within groove 64, as shown in FIGS. 11 and 12, for provisional capture of screw shaft assembly 12 with head assembly 13, as described herein. Ring 36 is expandable from the contracted and/or capture orientation to the expanded orientation for assembly of screw shaft assembly 12 with head assembly 13, as shown and described for example with regard to FIGS. 9-14.

Figure 14:
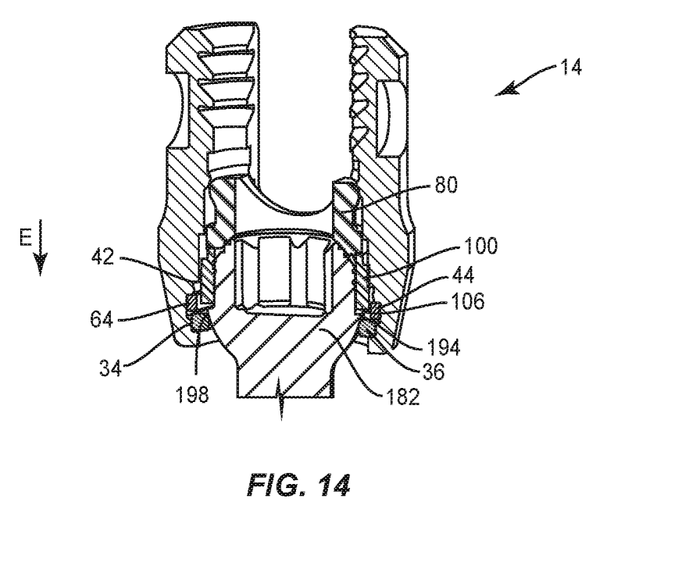
FIG. 14 is a perspective cross section view of components of the system shown in FIG. 9.

Ring 44 is disposable in a contracted orientation within groove 42, as shown in FIGS. 9-13, and resiliently biased to an expanded interference orientation within groove 64, as shown in FIG. 14. In the interference orientation, ring 44 is disposed in channel 66 and adjacent to ring 36 for abutting and/or contacting engagement therewith to resist and/or prevent translation of ring 36 from groove 34 into groove 64, and fixed connection of the components of bone fastener 180 including permanent capture of head assembly 13 and screw shaft assembly 12, as described herein.

Receiver 14 includes a surface 70. Surface 70 defines a slot 72. Slot 72 is configured for disposal of a part, such as, for example a crown 80 and a part, such as, for example, sleeve 100. In some embodiments, all or only a portion of surface 70 may have alternate surface configurations, such as, for example, rough, arcuate, undulating, mesh, porous, semi-porous, dimpled and/or textured.

Figure 2:
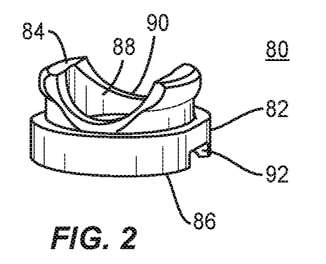
FIG. 2 is a perspective view of components of the system shown in FIG. 1.

Crown 80 is configured for disposal within cavity 20 and slot 72. Crown 80 includes a circumferential wall 82 having an end surface 84 and an end surface 86, as shown in FIG. 2. Surface 84 is configured to define at least a portion 88 of cavity 20. Portion 88 is defined by an outer surface 90 that defines a curved portion of crown 80 configured for engagement with a spinal implant, such as, for example, a spinal rod. Surface 90 is configured to provide an axial grip with a spinal implant, such as, for example, a spinal rod. Crown 80 is configured to provide flexion and/or extension strength to facilitate movement of the spinal rod. In some embodiments, crown 80 includes and/or is fabricated from commercially pure titanium. In some embodiments, all or only a portion of surface 90 may have alternate cross section configurations, such as, for example, oval, oblong triangular, square, polygonal, irregular, uniform, non-uniform, offset, staggered, and/or tapered.

Surface 84 defines a circumferential flange 200. Receiver 14 includes an undercut surface that defines a groove 202. Flange 200 is configured for disposal with groove 202, as shown in FIG. 6. Engagement of flange 200 with the undercut surface that defines groove 202 retains crown 80 with receiver 14 in a first orientation adjacent ring 44 when ring 44 is disposed in groove 42. Translation of crown 80, as described herein with regard to FIGS. 12-14, into a second orientation moves ring 44 from groove 42.

Surface 86 defines a pair of recesses 92 circumferentially disposed about crown 80. Recesses 92 are configured to facilitate engagement of crown 80 with a part, such as, for example, sleeve 100, as described herein. Recess 92 is substantially U-shaped. The wall portions of surface 86 that define recess 92 taper inwardly to capture sleeve 100, as described herein. In some embodiments, recess 92 may have alternate configurations, such as, for example, closed, V-shaped, W-shaped, oval, oblong triangular, square, polygonal, irregular, uniform, non-uniform, offset, staggered, flared and/or non-tapered. In some embodiments, surface 86 defines one or a plurality of recesses 92.

Figure 3:
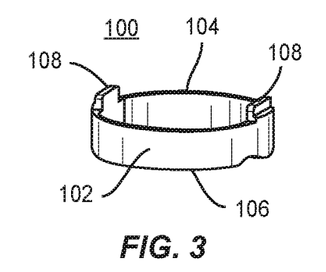
FIG. 3 is a perspective view of components of the system shown in FIG. 1.
Figure 4:
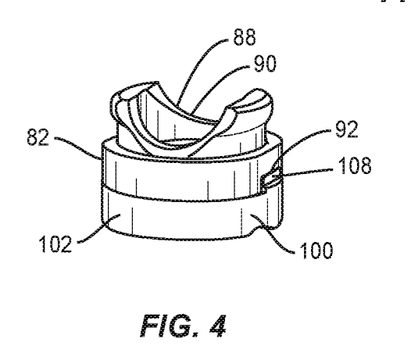
FIG. 4 is a perspective view of components of the system shown in FIG. 1.
Figure 5:
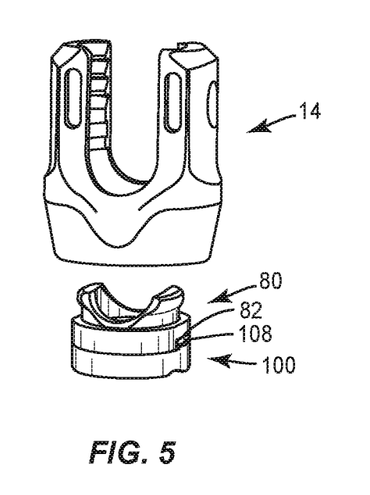
FIG. 5 is a perspective view of components of the system shown in FIG. 1.

Sleeve 100 includes a circumferential wall 102 having an end surface 104 and an end surface 106, as shown in FIG. 3. Surface 104 includes a pair of flared projections 108. Projections 108 are configured for a snap-fit engagement with the wall portions of surface 86 that define recess 92, as shown in FIG. 4, to fixedly attached sleeve 100 with crown 80. Sleeve 100 is configured to provide rigidity in the connection of sleeve 100 and screw shaft assembly 12 to facilitate manipulation of patient anatomy, for example, vertebrae. In some embodiments, sleeve 100 includes and/or is fabricated from chromium cobalt. In some embodiments, projection 108 may engage recess 92 to attach sleeve 100 with crown 80 in various fixation configurations, such as, for example, pop-fit, friction fit, pressure fit, locking keyway and/or adhesive. In some embodiments, projections 108 may have alternate configurations, such as, for example, closed, V-shaped, W-shaped, oval, oblong triangular, square, polygonal, irregular, uniform, non-uniform, offset, staggered, and/or tapered. In some embodiments, surface 104 defines one or a plurality of projections 108.

Sleeve 100 is configured for translation within slot 72 along surface 70. Translation of sleeve 100 within slot 72 causes surface 106 to engage ring 44. Surface 106 is disposed adjacent ring 44 such that axial translation of sleeve 100 displaces ring 44 from groove 42. Ring 44 is disengageable from groove 42 upon engagement with sleeve 100, which causes surface 46 to disengage from projection 50 and drives ring 44 from groove 42. As such, ring 44 is movable between the contracted orientation and the expanded interference orientation in groove 64, as described herein, to prevent migration of ring 36 from groove 34 into groove 64 for fixed connection of the components of bone fastener 180. Surface 106 is positioned with ring 44 to resist and/or prevent displacement of ring 44 from channel 66.

Screw shaft assembly 12 includes shaft 181 and head 182. Shaft 181 is configured to penetrate tissue, such as, for example, vertebral tissue. In some embodiments, shaft 181 includes an outer surface having an external thread form. In some embodiments, the external thread form may include a single thread turn or a plurality of discrete threads. Head 182 includes a tool engaging portion 184 configured to engage a surgical tool or instrument, as described herein. In some embodiments, portion 184 includes a hexagonal cross-section. In some embodiments, portion 184 may have alternative cross-sections, such as, for example, rectangular, polygonal, hexalobe, oval, or irregular. Head 182 includes a surface 186 that defines a plurality of ridges 188 to improve purchase of head 182 with crown 80. In some embodiments, head 182 includes an outer surface 190 having planar surfaces or flats and/or arcuate surfaces.

Surface 190 defines protrusion, such as, for example, a ridge 194. Ridge 194 extends circumferentially about head 182. Ridge 194 includes a surface 196 and a surface 198 configured for engagement with ring 36. As head 182 axially translates along receiver 14, surface 196 engages ring 36 causing ring 36 to translate into groove 64 to an expanded orientation, as described herein. As head 182 translates further into receiver 14, ring 36 passes over ridge 194 and resiliently contracts about head 182 within channel 66 to provisionally capture screw shaft assembly 12, as shown in FIG. 12. As head 182 translates in an opposite direction, surface 198 engages ring 36 to drive ring 36 from groove 64 into groove 34, as described herein. Surface 198 is configured to resist and/or prevent disengagement of ring 36 from groove 34 for permanent capture of head assembly 13 and screw shaft assembly 12 in a configuration having a range of motion that is restricted to a single plane. In some embodiments, head 182 includes planar side surfaces to enable uni-axial movement when the components of bone fastener 180 are assembled.

In some embodiments, screw shaft assembly 12 is manually engageable with head assembly 13 in a non-instrumented assembly, as described herein. In some embodiments, manual engagement and/or non-instrumented assembly of head assembly 13 and screw shaft assembly 12 includes coupling without use of separate and/or independent instrumentation engaged with screw shaft assembly 12 components to effect assembly. In some embodiments, manual engagement and/or non-instrumented assembly includes a practitioner, surgeon and/or medical staff grasping head assembly 13 and screw shaft assembly 12 and forcibly assembling the components. In some embodiments, manual engagement and/or non-instrumented assembly includes a practitioner, surgeon and/or medical staff grasping head assembly 13 and screw shaft assembly 12 and forcibly snap fitting the components together, as described herein. In some embodiments, manual engagement and/or non-instrumented assembly includes a practitioner, surgeon and/or medical staff grasping head assembly 13 and screw shaft assembly 12 and forcibly pop fitting the components together and/or pop fitting head assembly 13 onto screw shaft assembly 12, as described herein. In some embodiments, a force in a range of 2-50 N is required to manually engage head assembly 13 and screw shaft assembly 12 and forcibly assemble the components. For example, a force in a range of 2-50 N is required to snap fit and/or pop fit assemble head assembly 13 and screw shaft assembly 12. In some embodiments, a force in a range of 5-10 N is required to manually engage head assembly 13 and screw shaft assembly 12 and forcibly assemble the components. For example, a force in a range of 5-10 N is required to snap fit and/or pop fit assemble head assembly 13 and screw shaft assembly 12. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, receiver 14 may be disposed with head 182 in alternate fixation configurations, such as, for example, friction fit, pressure fit, locking protrusion/recess, locking keyway and/or adhesive.

In some embodiments, spinal implant system 10 comprises a spinal implant kit, as described herein, which includes a plurality of screw shaft assemblies 12 and/or head assemblies 13. Screw shaft assembly 12 and/or head assembly is configured for selection such that the components of bone fastener 180 are interchangeable in a configuration having a range of motion that is restricted to a single plane.

In assembly, operation and use, spinal implant system 10, similar to the systems and methods described herein, includes a screw shaft assembly 12 for connection with a head assembly 13, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, a screw shaft assembly 12 is selected from a kit of a plurality of screw shaft assemblies 12 for interchangeable connection with head assembly 13 to comprise a bone fastener having uni-axial movement and/or a range of motion that is restricted to a single plane. In some embodiments, the kit of screw shaft assemblies 12 includes a variety of screw shaft assemblies having different movement configurations when assembled with an interchangeable head assembly 13, such as, for example, multi-axial movement, sagittal angulation movement, fixed axis movement, mono-axial movement and/or uni-planar movement.

Figure 8:
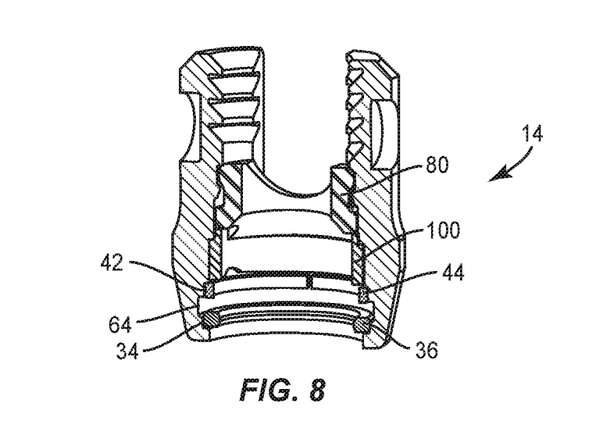
FIG. 8 is a perspective cross section view of components of the system shown in FIG. 6.

In some embodiments, head assembly 13 includes receiver 14 assembled with crown 80, sleeve 100, ring 44 and ring 36, as shown in FIGS. 5-8. In some embodiments, crown 80 is engaged with sleeve 100 by connection of projections 108 with recesses 92, as described herein. In some embodiments, ring 44 is initially disposed with groove 42 in a contracted orientation, as shown in FIG. 7. In some embodiments, ring 36 is initially disposed with groove 34 in a contracted orientation, as shown in FIG. 8.

Screw shaft assembly 12 is manually engageable, as described herein, with head assembly 13, as shown in FIGS. 9-14. Head assembly 13 is assembled with screw shaft assembly 12 by translating receiver 14, in a direction shown by arrow A in FIG. 9. Engagement of head 182 with receiver 14 causes surface 196 to engage ring 36. Surface 196 causes ring 36 to translate ring 36, in a direction shown by arrow B in FIG. 10, such that ring 36 is positionable and allowed to expand into groove 64 to an expanded orientation, as described herein, Diameter D3 of groove 64 is larger than diameter D1 of groove 34 to allow ring 36 to expand into channel 66. Engagement of surface 196 with an inner surface of ring 36 causes ring 36 to expand and slide along ramp 69 into channel 66. As head 182 translates further into receiver 14, ring 36 passes over ridge 194 and resiliently contracts about head 182 within channel 66 to provisionally capture screw shaft assembly 12, as shown in FIG. 12.

Screw shaft assembly 12 is translated, in a direction shown by arrow C in FIG. 12, to seat screw shaft assembly 12 with receiver 14. Translation of head 182 causes surface 198 to engage ring 36. Surface 198 causes ring 36 to translate, in a direction shown by arrow D in FIG. 13, to drive ring 36 from groove 64 into groove 34. Ring 36 axially translates along receiver 14 and/or slides along ramp 69 into groove 34. In some embodiments, surface 198 is positioned with ring 36 to resist and/or prevent displacement of ring 36 from groove 34.

Crown 80 and sleeve 100 are manipulated, for example, via engagement by a surgical instrument to translate crown and sleeve 100, in a direction shown by arrow E in FIG. 14. Surface 106 engages ring 44 such that surface 46 disengages from projection 50 and ring 44 is displaced from groove 42, as shown in FIG. 14. Ring 44 translates into groove 64 and resiliently expands into channel 66 to an expanded, interference orientation, as described herein. Ring 44 is oriented for abutting and/or contacting engagement with ring 36 to resist and/or prevent translation of ring 36 from groove 34 into groove 64, and fixed connection of the components of bone fastener 180 including permanent capture of head assembly 13 and screw shaft assembly 12 in a configuration having a range of motion that is restricted to a single plane, for example, in a uni-axial movement configuration. Surface 106 is positioned with ring 44 to resist and/or prevent displacement of ring 44 from channel 66.

In use, for treatment of a spinal disorder, bone fastener 180 including assembled screw shaft assembly 12 and head assembly 13 can be threaded and engaged with tissue. In some embodiments, bone fastener 180 is disposed adjacent vertebrae at a surgical site and is manipulated to drive, torque, insert or otherwise connect shaft 181 with vertebrae in connection with a surgical procedure, as described herein. In some embodiments, crown 80 includes a surface fabricated from commercially pure titanium for engagement with a spinal rod disposed with receiver 14 to provide an axial grip and flexion and/or extension strength to facilitate movement of the spinal rod. In some embodiments, sleeve 100 includes a surface fabricated from chromium cobalt to provide rigidity in the connection of sleeve 100 and screw shaft assembly 12 to facilitate manipulation of vertebrae.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 180 such as those described herein and/or fixation elements, which may be employed with a single vertebral level or a plurality of vertebral levels. In some embodiments, bone fasteners 180 may be engaged with vertebrae in various orientations, such as, for example, series, parallel, offset, staggered and/or alternate vertebral levels. In some embodiments, bone fasteners 180 may be configured as multi-axial screws, sagittal angulation screws, pedicle screws, mono-axial screws, uniplanar screws, fixed screws, anchors, tissue penetrating screws, conventional screws, expanding screws. In some embodiments, bone fasteners 180 may be employed with wedges, anchors, buttons, clips, snaps, friction fittings, compressive fittings, expanding rivets, staples, nails, adhesives, posts, connectors, fixation plates and/or post.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a first member comprising an inner surface defining an implant cavity and a plurality of adjacent grooves, the first member comprising a projection extending outwardly from the inner surface;
   a first band configured for disposal within the grooves;
   a second band comprising a body defining a recess configured for disposal of the projection to resist movement of the second band relative to the inner surface;
   a second member configured to penetrate tissue and including a head engageable with the first band to provisionally connect the members;
   a first part engageable with a spinal rod disposed with the implant cavity; and
   a second part attached with the first part and being engageable with the second band to remove the projection from the recess and dispose the second band adjacent the first band to fix connection of the members.

2. A bone fastener as recited in claim 1, wherein the fixed connection of the members includes relative movement in a single plane.

3. A bone fastener as recited in claim 1, wherein the members are connected in a uni-axial screw configuration.

4. A bone fastener as recited in claim 1, wherein the second part includes cobalt chromium.

5. A bone fastener as recited in claim 1, wherein the first part includes a circumferential wall engageable with the inner surface of the first member, the wall including at least one recess.

6. A bone fastener as recited in claim 1, wherein the second part interfaces with the second member to restrict relative movement between the members to a single plane.

7. A bone fastener as recited in claim 1, wherein the second part includes a circumferential wall engageable with the inner surface of the first member and the second band, the wall including at least one flared projection.

8. A bone fastener as recited in claim 1, wherein the second part includes a pair of flared projections engageable with a pair of recesses of the first part.

9. A bone fastener as recited in claim 1, wherein the grooves include a first groove, a second groove and a third groove that are circumferentially disposed with the inner surface of the first member and along a longitudinal axis thereof.

10. A bone fastener as recited in claim 9, wherein the third groove has a larger diameter relative to the first groove and the second groove.

11. A bone fastener as recited in claim 1, wherein the head is manually engageable with the first band to connect the members in a non-instrumented assembly.

12. A bone fastener as recited in claim 1, wherein the first band is expandable between a provisional capture orientation and an expanded orientation, and the second band is expandable between a contracted orientation and an interference orientation to fix connection of the members.

13. A bone fastener as recited in claim 1, wherein the projection is positioned within one of the plurality of adjacent grooves.

14. A bone fastener comprising:
    a first member comprising an inner surface defining an implant cavity and a plurality of adjacent grooves including a first portion and a second portion having a greater diameter than the first portion, the first member comprising a projection extending outwardly from the inner surface;
    a first band and a second band configured for disposal within the grooves in an expanded configuration in the second portion and a contracted configuration in the first portion, the second band comprising a body defining a recess configured for disposal of the projection when the bands are in the contracted configuration to resist movement of the second band relative to the inner surface;
    a second member configured to penetrate tissue and including a head engageable with the first band to connect the members;
    a first part engageable with a spinal rod disposed with the implant cavity; and
    a second part attached with the first part and being engageable with the second band to remove the projection from the recess and dispose the second band adjacent the first band, the head being engageable with the second part to limit relative movement in a single plane.

15. A bone fastener as recited in claim 14, wherein the second part includes a circumferential wall engageable with the inner surface of the first member and the second band, the wall including at least one flared projection.

16. A bone fastener as recited in claim 14, wherein the first portion includes a first groove and a third groove that are circumferentially disposed with the inner surface of the first member, and the second portion includes a second groove disposed between the first groove and the third groove.

17. A bone fastener as recited in claim 14, wherein the grooves are disposed in a serial orientation along a longitudinal axis of the first member.

18. A bone fastener as recited in claim 14, wherein the first band is expandable between a provisional capture orientation and an expanded orientation, and the second band is expandable between a contracted orientation and an interference orientation to fix connection of the members.

19. A bone fastener comprising:
   a first member comprising an inner surface defining an implant cavity and a plurality of adjacent grooves including a first groove, a second groove and a third groove, the second groove having a greater diameter than the first groove and the third groove, the first member comprising a projection extending outwardly from the inner surface, the projection being positioned within the third groove;
   a first expandable band configured for disposal within the grooves;
   a second expandable band comprising a body defining a recess configured for disposal of the projection to resist movement of the second band relative to the inner surface;
   a second member configured to penetrate tissue and including a head engageable with the first band for translation from the first groove to the second groove to provisionally connect the members;
   a first part engageable with a spinal rod disposed with the implant cavity; and
   a second part attached with the first part and engageable with the second band to remove the projection from the recess as the second band translates from the third groove to the second groove such that the second band prevents the first band from translating back into the second groove to fix connection of the members for relative movement in a single plane.

20. A bone fastener as recited in claim 19, wherein the head is manually engageable with the first band to connect the members in a non-instrumented assembly.

* * * * *